(12) United States Patent
Kaur et al.

(10) Patent No.: US 8,846,013 B2
(45) Date of Patent: Sep. 30, 2014

(54) TOPICAL APPLICATION OF 1-HYDROXYL-3,5-BIS(4'HYDROXY STYRYL)BENZENE

(75) Inventors: Simarna Kaur, Watchung, NJ (US); Michael D. Southall, Lawrenceville, NJ (US); Robert A. Zivin, Miami, FL (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 13/537,959

(22) Filed: Jun. 29, 2012

(65) Prior Publication Data

US 2014/0004066 A1    Jan. 2, 2014

(51) Int. Cl.
| | |
|---|---|
| A61K 8/00 | (2006.01) |
| A61K 8/18 | (2006.01) |
| A61Q 5/08 | (2006.01) |
| A61Q 19/02 | (2006.01) |
| C07C 39/12 | (2006.01) |
| C07C 39/16 | (2006.01) |

(52) U.S. Cl.
USPC .............................. 424/62; 568/717; 568/718

(58) Field of Classification Search
None
See application file for complete search history.

(56) References Cited

U.S. PATENT DOCUMENTS

| | | | |
|---|---|---|---|
| 5,804,572 | A | 9/1998 | Blank et al. |
| 6,414,037 | B1 | 7/2002 | Pezzulo et al. |
| 6,653,327 | B2 | 11/2003 | Majeed et al. |
| 7,288,513 | B2 | 10/2007 | Taylor et al. |
| 7,745,670 | B2 | 6/2010 | DiMauro |
| 7,985,776 | B2 | 7/2011 | Lilienfeld et al. |
| 2003/0113388 | A1 | 6/2003 | Phan |
| 2008/0075671 | A1 | 3/2008 | Di Mauro |
| 2008/0076821 | A1 | 3/2008 | Di Mauro |
| 2009/0087385 | A1 | 4/2009 | Di Mauro |
| 2009/0325963 | A1 | 12/2009 | Lilienfeld et al. |
| 2010/0087527 | A1 | 4/2010 | Di Mauro |
| 2010/0190803 | A1 | 7/2010 | Shin et al. |
| 2010/0292512 | A1 | 11/2010 | DiMauro |
| 2011/0081430 | A1 | 4/2011 | Kaur et al. |
| 2011/0081431 | A1 | 4/2011 | Kaur et al. |
| 2011/0081433 | A1 | 4/2011 | Kaur et al. |
| 2011/0257587 | A1 | 10/2011 | Lilienfeld et al. |
| 2012/0101156 | A1 | 4/2012 | Oddos |

FOREIGN PATENT DOCUMENTS

| | | |
|---|---|---|
| KR | 2010-135577 | 12/2010 |
| WO | WO 99/55352 | 11/1999 |
| WO | 2004/031122 | 4/2004 |
| WO | 2007/080053 | 7/2007 |

OTHER PUBLICATIONS

Ando et al., Quasi-Drugs Developed in Japan for the Prevention or Treatment of Hyperpigmentary Disorders, Int. J. Mol. Sci., 2010, 11 (2566-2575).
Chen,"SIRT1 Protects Against Microglia-dependent Amyloid-B toxicity Through Inhibiting NF-KB Signaling", J. Biol. Chem., (2005); vol. 280(48), pp. 40364-40374.
Handbook of Non-Invasive Methods and the Skin, eds. J. Serup, G. Jemec & G. Grove, Chapter 66.1 (2006) 579-582.
Kim, "Reservatrol Inhibits Inducible Nitric Oxide Synthase and Cycloozygenase-2 Expression in β-amyloid-treated C6 Glioma Cells"; Int. J. Mol. Med., (2006), vol. 17, pp. 1069-1075.
Solano et al., Hypopigmenting agents: an updated review on biological, chemical and clinical aspects, Pigment Cell Res. 19, 2006, (550-571).
VINIFEROL® Grapevine Shoot Extract for Cosmetics, Breko GmbH, 1977.
Zhang et al., "Hydrangeic acid from the processed leaves of *Hydrangea macrophylla* var. thunbergii as a new type of anti-diabetic compound", European Journal of Pharmacology, 606 (2009) 255-261.
Weber et al., Activation of NFkB is inhibited by curcumin and related enones. Bioorganic & Medicinal Chemistry 14 ( 2006) 2450-2461.
In re the U.S. Appl. No. 13/538,017 the Restriction Requirement dated Apr. 29, 2013.
In re the U.S. Appl. No. 13/538,017 the non-final rejection dated Jun. 27, 2013.
In re the U.S. Appl. No. 13/538,054 the non-final rejection dated Mar. 13, 2013.
In re the U.S. Appl. No. 13/538,054 the Notice of Allowance dated Aug. 22, 2013.
In re the U.S. Appl. No. 13/538,101 the Restriction Requirement dated Apr. 26, 2013.
In re the U.S. Appl. No. 13/538,101 the non-final rejection dated Jul. 5, 2013.
CAS Registry No. 14938-35-3, received Sep. 20, 2013.
Jang et al., "Inhibitory effects of curcuminoids from *Curcuma longa* on matrix metalloproteinase-1 expression in keratinocytes and fibroblasts", Journal of Pharmaceutical Investigation, Jan. 20, 2012, Author's personal copy.

*Primary Examiner* — Scott Long
*Assistant Examiner* — Sarah Alawadi

(57) ABSTRACT

The present invention relates to compositions comprising 1-hydroxyl 3,5-bis(4'hydroxyl styryl)benzene or a cosmetically acceptable salt thereof, and methods of treating human skin and signs of skin aging using said compositions.

8 Claims, No Drawings

TOPICAL APPLICATION OF 1-HYDROXYL-3,5-BIS(4'HYDROXY STYRYL)BENZENE

SEQUENCE LISTING

The instant application contains a Sequence Listing which has been submitted in ASCII format via EFS-Web and is hereby incorporated by reference in its entirety. Said ASCII copy, created on Jul. 30, 2012, is named JCO5062U.txt and is 1,213 bytes in size.

FIELD OF THE INVENTION

The invention relates to compositions and methods for the topical application of 1-hydroxyl 3,5-bis(4'hydroxyl styryl) benzene.

BACKGROUND OF THE INVENTION

It is known to provide active agents to the skin for purposes of treating the signs of skin aging, providing anti-inflammatory benefits to the skin, or lightening the skin.

A particular class of anti-inflammatory agents is those that inhibit the cell transcription factor nuclear kappa-B (NFκB). For example, it is known that certain substituted resorcinols such as 4-hexyl resorcinol and tetrahydrocurcuminoids are NFκB inhibitors. Such compounds provide anti-aging benefits when applied to the skin. However, only a relatively small group of compounds have been identified as both effective and cosmetically acceptable.

SUMMARY OF THE INVENTION

The inventors have now surprisingly found that 1-hydroxyl 3,5-bis(4'hydroxyl styryl)benzene is a potent NFκB inhibitor.

In one aspect, the invention provides a composition comprising 1-hydroxyl 3,5-bis(4'hydroxyl styryl)benzene or a cosmetically acceptable salt thereof; and a cosmetically acceptable topical carrier comprising an ingredient selected from the group consisting of wetting agents, emulsifiers, emollients, humectants, and fragrances.

The invention further provides a method of treating human skin, comprising topically applying to said human skin a composition comprising 1-hydroxyl 3,5-bis(4'hydroxyl styryl)benzene or a cosmetically acceptable salt thereof.

The invention also provides a method of treating a sign of skin aging, comprising topically applying to skin in need of such treatment a composition comprising 1-hydroxyl 3,5-bis (4'hydroxyl styryl)benzene or a cosmetically acceptable salt thereof.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Products described herein may optionally be in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin to treat the signs of skin aging as discussed infra. Such instructions may be printed on the container, label insert, or on any additional packaging.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "skin in need of treatment for the signs of aging" means a skin that is, but not limited to, sagging, loose, lax, rough, wrinkly, thinned, or uneven. Improving the signs of aging means improving the firmness of the skin, improving the texture of the skin, improving the appearance of wrinkles in skin, improving the skin tone, or the treating external aggressions in skin.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook of Non-Invasive Methods and the Skin, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle formation in skin. As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "treatment of external aggressions in skin" means the reduction or prevention of the damage from external aggressions in skin. Examples of external aggressions include, but are not limited to, damage to the skin from the use of cleansers (e.g., topical cleansers containing surfactants), make-up, shaving as well as environmental damage such as from UV light (e.g., sundamage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "improving the skin tone" means the lightening of the appearance of the skin (e.g., lightening pigmented marks or lesions, reducing skin sallowness, and/or evening the color of the skin).

As used herein, "skin in need of reducing skin inflammation" means a skin exhibiting redness or erythema, edema, or being reactive or sensitive to external elements. External elements include, but are not limited to, sun rays (UV, visible, IR), microorganisms, atmospheric pollutants such as ozone, exhaust pollutants, chlorine and chlorine generating compounds, cigarette smoke, cold temperature, heat Inflammatory disorders and related conditions which may be treated or prevented by use of the compositions of this invention include, but are not limited to the following: arthritis, bronchitis, contact dermatitis, atophic dermatitis, psoriasis, seborrheic dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, postinflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, insect bites, folliculitus, alopecia, and secondary conditions and the like.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, unless otherwise specified, all percentages of ingredients in compositions are weight percent of active/solids ingredient based on the total weight of composition.

Compositions of the present invention are suitable for treating human skin, e.g., skin on the face or body, for signs of skin aging, or for inflammation. In a particularly preferred embodiment, a composition according to the invention is used to treat the presence of lines and wrinkles and/or loss of elasticity.

1-Hydroxyl 3,5-bis(4'hydroxyl styryl)benzene

Compositions of the present invention comprise 1-hydroxyl 3,5-bis(4'hydroxyl styryl)benzene or a cosmetically acceptable salt thereof.

1-Hydroxyl 3,5-bis(4'hydroxyl styryl)benzene is a curcumin analog having the structure below:

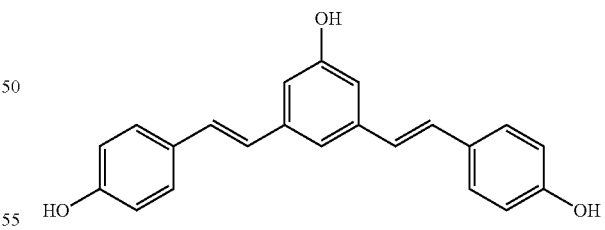

As described in U.S. Pat. No. 7,745,670, 1-hydroxyl 3,5-bis(4'hydroxyl styryl)benzene can be made by reacting 1-(bromomethyl)-4-methoxybenzene with triethyl phosphate using an Arbuzov reaction to produce diethyl [(4-methoxyphenyl)methyl]phosphonate. This is coupled with 5-methoxybenzene-1,3-dicarbaldehyde-using sodium hydride as base in THF, followed by reaction with boron trichloride and dichloromethane to replace methoxy groups with hydroxyls.

Salts of 1-hydroxyl 3,5-bis(4'hydroxyl styryl)benzene can be made by, for example, reacting the 1-hydroxyl 3,5-bis (4'hydroxyl styryl)benzene with a base such as piperazine, or another base, to produce at least some phenoxide salt of 1-hydroxyl 3,5-bis(4'hydroxyl styryl)benzene.

Topical Compositions

Generally, the 1-hydroxyl 3,5-bis(4'hydroxyl styryl)benzene or salt thereof is present in the composition in a cosmetically effective amount, such as from about 0.01% to about 10%, preferably from about 0.1% to about 5%, more preferably from about 0.2% to about 2%, even more preferably from about 0.5% to about 1.5%, by weight of the composition.

The compositions of the present invention are applied topically to human skin and/or hair.

The compositions may be spreadable. They may be topically applied by spreading, for example spreading over the skin or hair, in particular over skin of the face or hands.

In one embodiment, a composition of the invention is topically applied without a voltage.

In addition to 1-hydroxyl 3,5-bis(4'hydroxyl styryl)benzene, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically acceptable topical carrier includes water.

The cosmetically acceptable topical carrier may be unsuitable for ingestion.

The cosmetically acceptable topical carrier may include an ingredient selected from one or more of the following five classes: wetting agents, emulsifiers, emollients, humectants, and fragrances. In certain embodiments, the cosmetically acceptable topical carrier includes ingredients from two or more of the above-mentioned classes, such as ingredients from at least three or more of such classes.

In one embodiment, the cosmetically acceptable topical carrier includes water, an emulsifier, and an emollient.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to, solutions, suspensions, emulsions such as microemulsions and nanoemulsions, gels, solids and liposomes.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include humectants (e.g., water-retaining or hygroscopic materials) such as propylene glycol, pentylene glycol, polyethylene glycol, polypropylene glycol, glycerol, 1,2,4-butanetriol, sorbitol esters, 1,2,6-hexanetriol; as well as ethanol, and mixtures thereof. Solutions can optionally include a wetting agent, such as to provide foam, e.g, an anionic, non-ionic, or cationic wetting agent.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include hydrophobic compounds such as vegetable oils, mineral oils (e.g., petrolatum), fatty esters (e.g., isopropyl palmitate, c12-c15 alkyl benzoate) including those fatty esters of glycerol, silicone oils (e.g., dimethicone) and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Although it is preferred that the composition of the present invention includes water, the composition may alternatively be anhydrous or an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening (gelling) agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of suitable emulsifiers include those typically identified as such in the art of personal care and cosmetic formulations, e.g., cationic emulsifiers such as disteryldimonium chloride, non-ionic emulsifiers such as stereth-2, stereth-21; anionic emulsifiers such as potassium cetyl phosphate; polymeric emulsifiers such as acryloyldimethyltaurate/VP copolymers, and the like.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, (cross-linked) acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Active Agents

In one embodiment, the composition includes an additional NFκB-inhibitor such as a substituted resorcinol, (E)-3-(4-methylphenylsulfonyl)-2-propenenitrile (such as "Bay 11-7082," commercially available from Sigma-Aldrich of St. Louis, Mo.), a tetrahydrocurcuminoid (such as Tetrahydrocurcuminoid CG, available from Sabinsa Corporation of Piscataway, N.J.), paulownin, extracts of *Paulownia* wood (for example the wood of *Paulownia tomentosa, Paulownia fortunei, Paulownia elongate, Paulownia taiwaniana*, and/or *Paulownia kawakamii*), and combinations thereof.

In one embodiment, the composition further contains another cosmetically active agent. As used herein, a "cosmetically active agent" is a compound (e.g., a synthetic compound or a compound isolated from a natural source or a natural extract) that has a cosmetic or therapeutic effect on the skin including, but not limiting to anti-aging actives, anti-inflammatory agents, tropoelastin promoters, anti-acne agents, antimicrobial agents, anti-inflammatory agents, anti-mycotic agents, external analgesics, sunscreens, antioxidants, keratolytic agents, vitamins, skin lightening agents and skin firming agents.

In one embodiment, the composition includes a skin-lightening agent such as a tyrosinase inhibitor, melanin-degradation agent, melanosome transfer inhibiting agent including PAR-2 antagonists, retinoids, antioxidants, tranexamic acid, tranexamic acid cetyl ester hydrochloride, skin bleaching agent, linoleic acid, adenosine monophosphate disodium salt, Chamomilla extract, allantoin, opacifier, talc or silica, zinc salt, or the like, or other agent as described in Solano et al. Pigment Cell Res. 19 (550-571) and Ando et al. Int J Mol Sci 11 (2566-2575).

Examples of suitable tyrosinase inhibitors include but, are not limited to, vitamin C and its derivatives, vitamin E and its derivatives, kojic acid, arbutin, resorcinols, hydroquinone, flavones e.g., licorice flavanoids, licorice root extract, mulberry root extract, *dioscorea coposita* root extract, saxifraga extract and the like, ellagic acid, salicylates and derivatives, glucosamine and derivatives, fullerene, hinokitiol, dioic acid, acetyl glucosamine, 5,5'-dipropyl-biphenyl-2,2'-diol (magnolignan), 4-(4-hydroxyphenyl)-2-butanol (4-HPB), combinations of two or more thereof, and the like.

Examples of vitamin C derivatives include, but are not limited to, ascorbic acid and salts, ascorbic acid-2-glucoside, sodium ascorbyl phosphate, magnesium ascorbyl phosphate, and natural extract enriched in vitamin C.

Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives.

Examples of resorcinol derivatives include, but are not limited to, resorcinol, 4-substituted resorcinols like 4-alkyl-resorcinols such as 4-butyresorcinol (rucinol), 4-hexylresorcinol (SYNOVEA HR, SYNTHEON), phenylethyl resorcinol (SYMWHITE, SYMRISE), 1-(2,4-dihydroxyphenyl)-3-(2,4-dimethoxy-3-methylphenyl)-propane (nivitol, UNIGEN) and the like and natural extracts enriched in resorcinols.

Examples of salicylates include, but are not limited to, 4-methoxy potassium salicylate, salicylic acid, acetylsalicylic acid, 4-methoxysalicylic acid and their salts.

In certain preferred embodiments, the tyrosinase inhibitors include a 4-substituted resorcinol, a vitamin C derivative, or a vitamin E derivative. In more preferred embodiments, the tyrosinase inhibitor comprises phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents include PAR-2 antagonists such as soy trypsin inhibitor or Bowman-Birk Inhibitor, vitamin B3 and derivatives such as niacinamide, essential soy, whole soy, soy extract. In certain preferred embodiments, the melanosome transfer inhibiting agents includes a soy extract or niacinamide.

Examples of retinoids include, but are not limited to, retinol (vitamin A alcohol), retinal (vitamin A aldehyde), retinyl acetate, retinyl propionate, retinyl linoleate, retinoic acid, retinyl palmitate, isotretinoin, tazarotene, bexarotene, adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Other skin lightening agents include vitamin B5, vitamin B12, glycolic acid and extracts of *Paulownia* wood (for example the wood of *Paulownia tomentosa, Paulownia fortunei, Paulownia elongate, Paulownia taiwaniana*, and/or *Paulownia kawakamii*).

Other Materials

Various other materials may also be present in the composition, as known in the art. These include humectants, pH adjusters, chelating agents (e.g., EDTA), fragrances, dyes and preservatives (e.g., BHT, benzyl alcohol).

The composition and formulations and products containing such compositions of the present invention may be prepared using methodology that is well known by an artisan of ordinary skill.

Methods of Use

Compositions of the present invention may be topically applied to human skin, e.g., skin that is in need of treatment for one or more signs of skin aging as described above. In one embodiment, the compositions are applied to skin in need of treatment for lines and wrinkles and/or loss of elasticity. The compositions may be applied to the skin in need of such treatment according to a suitable treatment regimen, e.g., every month, every week, every other day, every day, twice a day, or the like.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example 1

NFκB-Inhibition

NFκB-INHIBITION TESTS were performed on various concentrations of 1-hydroxyl 3,5-bis(4'hydroxyl styryl)benzene and a vehicle control (DMSO). The 1-hydroxyl 3,5-bis(4'hydroxyl styryl)benzene was prepared as described in U.S. Pat. No. 7,745,670.

The NF-κB INHIBITION TEST was conducted as follows. Rat cardiac myoblasts H9c2 cells were purchased from ATCC (Manassas, Va.). Cultures were maintained in Dulbecco's modified Eagle's medium (DMEM, Invitrogen Life Technologies, Carlsbad, Calif.) supplemented with 10% fetal bovine serum, 100 units/ml penicillin, and 50 ug/ml streptomycin (Invitrogen life technologies, Carlsbad, Calif.). 1×10⁴ cells grown in 96-well plates were transiently transfected with 0.45 ug total DNA per well using Lipofectamine 2000 (Invitrogen life technologies, Carlsbad, Calif.). In all transfections, a construct with the thymidine kinase promoter and the Renilla luciferase reporter gene (pRL-TK, Promega, Madison Wis.) was included as an internal control in addition to the NF-kB luciferase promoter. One day after transfection, cells were treated with the indicated samples (in DMSO as vehicle) at indicated concentrations and stimulated with 100 ng/mL of Tumor Necrosis Factor-α (TNFα, Sigma-Aldrich, St Louis, Mo.) for approximately 24 hours before they were lysed for luciferase assays, using Dual-Luciferase Reporter System from Promega (Madison, Wis.), following manufacturer's protocol. Briefly, the firefly luciferase activity was measured first (representing NF-kB promoter activity), followed by the renilla luciferase (internal control), using luminometer LMAX, from Molecular Devices (Sunnyvale, Calif.). The ratio of these two luciferase activities (RLU) was used to evaluate the activity of each promoter:

NF-κB Inhibition=[1−(RLUsample/RLUcontrol)]*100 where RLUsample and RLUcontrol are the normalized luciferase activity ratios of the sample and control, respectively.

The results are shown in Table 1, in which NF-kB Gene Reporter Activation (Luminescence, L) is reported. Percent NF-kB Inhibition is also reported.

TABLE 1

|  | NF-kB Gene Reporter Activation (Luminescence, L) | Percent NF-kB Inhibition |
|---|---|---|
| Untreated | 131.5± | — |
| TNFα (100 ng/ml) Stimulated, "L$_{control}$" | 452.4 | — |
| TNFα + Vehicle (0.1% DMSO) | 588.3 | 0% |
| TNFα + 1-hydroxyl 3,5-bis(4'hydroxyl styryl)benzene (0.2 ug/ml) | 585.5± | 0.5% |
| TNFα + 1-hydroxyl 3,5-bis(4'hydroxyl styryl)benzene (0.5 ug/ml) | 458.6± | 22.1% |
| TNFα + 1-hydroxyl 3,5-bis(4'hydroxyl styryl)benzene (1 ug/ml) | 283.8± | 51.7% |
| TNFα + 1-hydroxyl 3,5-bis(4'hydroxyl styryl)benzene (2 ug/ml) | 170.5± | 71.0% |
| TNFα + 1-hydroxyl 3,5-bis(4'hydroxyl styryl)benzene (4 ug/ml) | 22.6± | 96.1% |

1-Hydroxyl 3,5-bis(4'hydroxyl styryl)benzene showed a strong reduction in NF-kB mediated inflammatory response in human skin cells.

Example 2

Anti-Inflammatory Activity

The topical anti-inflammatory activities of 1-hydroxyl 3,5-bis(4'hydroxyl styryl)benzene and its piperazine salt were evaluated as follows.

Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm²) with 1-hydroxyl 3,5-bis(4'hydroxyl styryl)benzene thereof in a 70:30 Ethanol-Propylene glycol vehicle two hours before exposure to solar ultraviolet light (1000W-Oriel solar simulator equipped with a 1-mm Schott WG 320 filter; UV dose applied: 70 kJ/m² as measured at 360 nm). The equivalents were incubated for 24 hours at 37° C. with maintenance medium then supernatants were analyzed for IL-8 cytokine release using commercially available kits (Millipore Corp., Billerica, Mass.).

The results are shown in Table 2.

TABLE 2

| Sample | Change over vehicle alone (Normalized to 100) | % inhibition over UV treatment |
|---|---|---|
| Vehicle (70/30: Ethanol + Propylene Glycol) | 100 ± 28 | — |
| Vehicle + UV | 134 ± 42 | — |
| UV + 1-hydroxyl 3,5-bis(4'hydroxyl styryl)benzene - Free Phenol (0.5%) | 82 ± 21 | 39% |
| UV + 1-hydroxyl 3,5-bis(4'hydroxyl styryl)benzene - Free Phenol (1%) | 80 ± 26 | 40% |
| UV + 1-hydroxyl 3,5-bis(4'hydroxyl styryl)benzene - Piperazine salt (0.5%) | 85 ± 14 | 37% |
| UV + 1-hydroxyl 3,5-bis(4'hydroxyl styryl)benzene - Piperazine salt (1%) | 81 ± 31 | 40% |

1-Hydroxyl 3,5-bis(4'hydroxyl styryl)benzene and its piperazine salt showed strong reduction in UV-induced inflammation in human skin cells.

Example 3

Induction of Elastin and Collagen1A Gene Expression

Primary human dermal fibroblasts (Lifeline Cell Technologies, Frederick, Md.) were grown until confluence in DMEM media (Invitrogen/Life Technologies, Carlsbad, 10 CA) with 10% FBS and 1% Penicillin-Streptomycin on 24 well tissue culture plates, followed by treatment with 1-hydroxyl 3,5-bis (4'hydroxyl styryl)benzene (0.1 ug/mL) with and without TNF-a for 48 hr. Post-treatment, cells were lysed using RLT buffer and total RNA was isolated using the RNeasy Mini Kit (Qiagen, Valencia, Calif.). Quantitative PCR was performed using the Gene Amp PCR System 9700 and 7500 Real Time PCR 15 System cycler (Applied Biosystems)/Life Technologies, Carlsbad, Calif.). Elastin (Qiagen) and Collagen1α1 primers (custom sequence-sense: 5'-TCC-CCA-GCT-GTC-TTA-TGG CT-3' (SEQ ID NO: 1) and anti-sense: 5'-CAG-GCA-CGG-AAA-TTC-CTC-C-3' (SEQ ID NO: 2)) were used. The housekeeping gene GAPDH was used for normalization (custom primer sequence: F 5'-ATC-TCT-GCC-CCC-TCT-GCT-G-3' (SEQ ID NO: 3) and R 5'-ATG-GTT-CAC-ACC-CAT-GAC-GA-3' (SEQ ID NO: 4); Invitrogen/Life Technologies, Carlsbad, Calif.). Fold-changes in PCR (normalized to 5 GAPDH) were calculated from untreated.

The results are shown in Tables 3A and 3B.

TABLE 3A

|  | Collagen 1A Normalized Fold-change in PCR (Mean) | Elastin Normalized Fold-change in PCR (Mean) |
|---|---|---|
| Untreated | 1.0 | 1.0 |
| 1-hydroxyl 3,5-bis(4'hydroxyl styryl) benzene (0.1 ug/mL) | 2.96 | 6.23 |

TABLE 3B

|  | Collagen 1A Normalized Fold-change in PCR (Mean) | Elastin Normalized Fold-change in PCR (Mean) |
|---|---|---|
| Untreated | 1.0 | 1.0 |
| TNF-α (10 ng/mL) | 0.52 | 0.41 |
| TNF-α (10 ng/mL) + 1-hydroxyl 3,5-bis (4'hydroxyl styryl)benzene (0.1 ug/mL) | 1.36 | 1.12 |

1-Hydroxyl 3,5-bis(4'hydroxyl styryl)benzene increased the expression of genes associated with collagen and elastin production.

Example 4

Inhibition of TNF-α-Induced MMP-9 Levels

The ability of 1-hydroxyl 3,5-bis(4'hydroxyl styryl)benzene to inhibit TNF-a induced MMP-9 levels was tested at different concentrations as follows. The formation of TNF-α induced MMP-9 is involved in the undesirable breakdown of extracellular matrix in human skin.

Epidermal equivalents (EPI 200 HCF) were purchased from MatTek (Ashland, Mass.). Upon receipt, the epidermal equivalents were incubated for 24 hours at 37° C. in maintenance medium without hydrocortisone. The equivalents were topically treated (2 mg/cm$^2$) with 1-hydroxyl 3,5-bis(4'hydroxyl styryl)benzene extracts in a 70% ethanol/30% propylene glycol vehicle 2 hours before treatment with TNF-α (100 ng/mL). the equivalents were incubated for 48 hours at 37° C. with maintenance medium then supernatants were analyzed for MMP-9 using commercially available kits (R&D Systems, Minneapolis, Minn.).

The results are shown in Table 4.

TABLE 4

| Treatment (Dose, as % w/v) | Mean of MMP-9 Release (ng/ml) | Percent Inhibition of MMP-9 Production (over TNF-a alone) |
|---|---|---|
| Untreated | 1422 ± 611 | - |
| TNF-α alone | 3557 ± 1181 | - |
| TNF-α + 1-hydroxyl 3,5-bis (4'hydroxyl styryl) benzene (0.25%) | 1392 ± 627 | 60.9 |
| TNF-α + 1-hydroxyl 3,5-bis (4'hydroxyl styryl)benzene (0.5%) | 1012 ± 249 | 71.6 |

1-Hydroxyl 3,5-bis(4'hydroxyl styryl)benzene inhibited the formation of TNF-α induced MMP-9.

Example 5

A composition according to the invention is prepared by blending the ingredients in Table 5.

TABLE 5

| Trade Name | INCI Name | % wt |
|---|---|---|
| Deionized Water | Water | 70.64 |
| Sodium Chloride | Sodium Chloride | 0.01 |
|  | 1-hydroxyl 3,5-bis(4'-hydroxyl styryl) benzene | 1.00 |
| Snow White Petrolatum | Petrolatum | 4.00 |
| ISOFOL 28 | Dodecylhexadecanol | 2.50 |
| DOW CORNING Q7-9120 (20 CS) | Dimethicone | 1.25 |
| KESSCO IPP | Isopropyl Palmitate | .00 |
| VARISOFT TA-100 | Distearyldimonium Chloride | 5.00 |
| Glycerin | Glycerin | 12.00 |
| Benzyl Alcohol | Benzyl Alcohol | 0.60 |

Water is added to a process vessel. Mixing is begun and salt is added and mixed until dissolved. Heat is applied and mixing continued until to 85° C. is reached. 1-hydroxyl 3,5-bis (4'-hydroxyl styryl)benzene is solublized in glycerin, then added while mixing is continued and the temperature is maintained at 85° C. Distearyldimonium chloride is added, along with petrolatum and dodecylhexadecanol, dimethicone, and isopropyl palmitate. The composition is mixed at 85° C. for another 10-15 minutes. The composition is then removed from heat, mixed and cooled. At 40° C., benzyl alcohol is added, q.s. with water, mixed and cooled to 30-35° C. The composition is then filled into packaging.

A composition according to the invention is prepared by blending the ingredients in Table 6.

TABLE 6

| Trade Name | INCI Name | % Wt |
|---|---|---|
| Deionized Water | Water | 70.55 |
| Snow White Petrolatum | Petrolatum | 4.00 |
| ISOFOL 28 | Dodecylhexadecanol | 2.50 |
| Dow Corning Q7-9120 (20 CS) | Dimethicone | 1.25 |
| BHT | BHT | 0.10 |
| Kessco IPP | Isopropyl Palmitate | 3.00 |
| Varis oft TA-100 | Distearyldimonium Chloride | 5.00 |
|  | 1-hydroxyl 3,5 -bis (4'hydroxyl styryl) benzene | 1.0 |
| Glycerin | Glycerin | 12.00 |
| Retinol 10S | *Gylcine Soja* (Soybean) Oil and Retinol | 1.00 |
| Benzyl Alcohol | Benzyl Alcohol | 0.60 |

Water is added to a process vessel and the temperature is set to 85° C. Mixing is begun and glycerin is added and mixed until dissolved. VARISOFT TA-100 is added, along with petrolatum and ISOFOL 28, DOW CORNING Q7-9120 20 CS, and isopropyl palmitate. The composition is mixed at 85° C. for another 10-15 minutes. The composition is then removed from heat, mixed and cooled.

A composition according to the invention is prepared by blending the ingredients in Table 7.

TABLE 7

| Trade Name | INCI Name | % Wt |
|---|---|---|
| Deionized Water | Water | 73 |
| HYDROLITE 5 | Pentylene glycol | 5 |
|  | 1-hydroxyl 3,5 -bis (4'-hydroxyl styryl) benzene | 5 |
| NATRULON OSF | *Carthamus Tinctorius* Oleosome | 10 |
| FINSOLV TN | C12-15 Alkyl Benzoate | 4 |
| ARISTOFLEX AVC | Ammonium Acryloyldimethyltaurate/VP Copolymer | 2 |

TABLE 7-continued

| Trade Name | INCI Name | % Wt |
|---|---|---|
| *Tanacetum parthenium* extract | *Chrysanthemum Parthenium* (Feverfew) Leaf/Flower/Stem Juice | 1 |

1-hydroxyl 3,5-bis(4'-hydroxyl styryl)benzene is weighed and dissolved in HYDROLITE 5 and deionized water is added to form Phase A. Oleosomes and FINSOLV TN are mixed to form Phase B. Phase B is added to Phase A very slowly under continuous mixing. Mixing is continued for 15 minutes until a uniform emulsion is formed. ARISTOFLEX AVC is added to the emulsion under continuous mixing at high speed to obtain a thick, smooth and homogenous formulation.

A composition according to the invention is prepared by blending the ingredients in Table 8.

TABLE 8

| Trade Name | INCI Name | % Wt |
|---|---|---|
| Deionized Water | Water | 67.70 |
| Carbomer | Cross-linked polyacrylic acid | 0.60 |
| VERSENE NA | Disodium EDTA | 0.20 |
| Brij 72 | Steareth-2 | 0.75 |
| Brij 721 | Steareth-21 | 1.50 |
| FINSOLV TN | C12-15 Alkyl Benzoate | 2.00 |
| Dimethicone NF | Dow corning Q7-9120 Silicone Fluid (20 cst) | 5.00 |
| PHENONIP XB | Phenoxyethanol, Methylparaben, Ethylparaben, Propylparaben | 1.00 |
| LYS' LASTINE | *Peucedanum graveolens* (10% active) | 10.00 |
| SYMMATRIX | Maltodextrin, *Rubus Fruticosus* (Blackberry) Leaf Extract (10% active) | 10.00 |

TABLE 8-continued

| Trade Name | INCI Name | % Wt |
|---|---|---|
| 1-hydroxyl 3,5-bis(4'-hydroxyl styryl)benzene | | 0.25 |
| Glycerin | Glycerin | 1.0 |

An oil phase is prepared by adding FINSOLV TN to a clean glass beaker. Agitation is begun and the vessel is heated to 55-60° C. When the oil phase reaches 55° C. or higher, Brij 72 and Brij 721 are added. When the oil phase reaches 55-60° C., it is held at that temperature and mixed for 15 min (or until uniform). The temperature is then held at 55-60° C. with mixing until addition to water phase.

A water phase is prepared by adding water to a clean glass beaker. Agitation is begun and the vessel is heated to 55-60° C. Disodium EDTA is added. At 55-60° C., the ingredients are mixed for 15 min or until homogeneous. The temperature is then held at 55-60° C. with mixing for phasing.

The oil phase is added to the water phase with increased agitation and then mixed at high speed for 10-20 min. At 50° C. or lower, dimethicone is added. At 40° C. or lower, PHENONIP XB is added. The phases are then mixed for 10 min or until uniform. Sodium hydroxide is added (target pH is 5.4). The composition is then mixed for 10 min or until uniform. LYS'LASTINE and SYMMATRIX are then added. 1-hydroxyl 3,5-bis(4'-hydroxyl styryl)benzene is weighed and dissolved in glycerin and added to the mixture, which is mixed until uniform. Water is then added to QS and the composition is mixed for 10 additional minutes.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

The invention claimed is:

1. A composition comprising:
   1-hydroxyl 3,5-bis(4'hydroxyl styryl)benzene or a cosmetically acceptable salt thereof, wherein the 1-hydroxyl 3,5-bis(4'hydroxyl styryl)benzene or a cosmetically acceptable salt provides NFκB inhibition;
   a sunscreen; and
   a cosmetically acceptable topical carrier comprising an ingredient selected from the group consisting of wetting agents, emulsifiers, emollients, humectants, and fragrances.

2. The composition of claim 1, wherein the cosmetically acceptable topical carrier comprises ingredients selected from at least two of the following classes: wetting agents, emulsifiers, emollients, humectants, and fragrances.

3. The composition of claim 1, wherein the cosmetically acceptable topical carrier comprises an emollient and an emulsifier.

4. The composition of claim 1, wherein the cosmetically acceptable topical carrier comprises ingredients selected from at least three of the following classes: wetting agents, emulsifiers, emollients, humectants, and fragrances.

5. The composition of claim 1, further comprising an additional NFκB-inhibitor.

6. The composition of claim 1, wherein the composition comprises about 0.01% to about 10% of said 1-hydroxyl 3,5-bis(4'hydroxyl styryl)benzene or salt thereof.

7. The composition of claim 1, further comprising a skin lightening agent.

8. A cosmetic composition for topical application to human skin or hair comprising 1-hydroxyl 3,5-bis(4'hydroxyl styryl)benzene or a cosmetically acceptable salt thereof; an emollient; and a sunscreen.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccccagctg tcttatggct                                                    20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggcacgga aattcctcc                                                     19

<210> SEQ ID NO 3
<211> LENGTH: 19
<212> TYPE: DNA
<213> ORGANISM: Artificial Sequence
<220> FEATURE:
```

```
-continued

<223> OTHER INFORMATION: Description of Artificial Sequence: Synthetic
      primer

<400> SEQUENCE: 3
atctctgccc cctctgctg                                              19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atggttcaca cccatgacga                                             20
```